(12) United States Patent
Matsumoto

(10) Patent No.: US 10,683,609 B2
(45) Date of Patent: Jun. 16, 2020

(54) MANIPULATION ROPE

(71) Applicant: TOKUSEN KOGYO CO., LTD., Ono, Hyogo (JP)

(72) Inventor: Keiji Matsumoto, Ono (JP)

(73) Assignee: TOKUSEN KOGYO CO., LTD., Ono, Hyogo (JP)

( * ) Notice: Subject to any disclaimer, the term of this patent is extended or adjusted under 35 U.S.C. 154(b) by 83 days.

(21) Appl. No.: 15/570,930

(22) PCT Filed: Apr. 22, 2016

(86) PCT No.: PCT/JP2016/062746
§ 371 (c)(1),
(2) Date: Oct. 31, 2017

(87) PCT Pub. No.: WO2016/208262
PCT Pub. Date: Dec. 29, 2016

(65) Prior Publication Data
US 2018/0105981 A1    Apr. 19, 2018

(30) Foreign Application Priority Data

Jun. 26, 2015  (JP) .................................. 2015-128519

(51) Int. Cl.
*D07B 1/10* (2006.01)
*D07B 1/06* (2006.01)
(Continued)

(52) U.S. Cl.
CPC ............. *D07B 1/10* (2013.01); *D07B 1/0673* (2013.01); *D07B 1/0693* (2013.01); *F16C 1/20* (2013.01);
(Continued)

(58) Field of Classification Search
CPC ...... D07B 1/10; D07B 1/0673; D07B 1/0693; D07B 1/0646; D07B 2201/2021; D07B 2201/2059; F16C 1/20; F16C 1/02
(Continued)

(56) References Cited

U.S. PATENT DOCUMENTS 4,738,096 A    4/1988  Hatakeyama et al.
5,475,973 A   12/1995  Furukawa et al.
(Continued)

FOREIGN PATENT DOCUMENTS

EP    0602733 A1   6/1994
JP    1-62396 U    4/1989
(Continued)

OTHER PUBLICATIONS

International Search Report dated Nov. 10, 2015 for corresponding JP Patent Application No. 2015-128519.

*Primary Examiner* — Shaun R Hurley
*Assistant Examiner* — Patrick J. Lynch
(74) *Attorney, Agent, or Firm* — Dickinson Wright PLLC

(57) ABSTRACT

A manipulation rope having an excellent torque transmittability is provided. A manipulation rope is a rope that is advantageously used as a manipulation rope for a medical instrument, and includes a side wire or a side strand which is an outermost layer, the side wire or the side strand having a forming rate that is greater than 100% and not greater than 110%. The side wire or the side strand having been formed has a spiral shape in which a flatness that is an aspect ratio obtained by a major axis being divided by a minor axis is preferably not less than 1.01 and preferably not greater than 1.10. Further, an elongation of the rope at a time when a tensile load that is 1.0% of a breaking load is applied, is preferably not less than 0.04% and preferably not greater than 0.10%.

6 Claims, 6 Drawing Sheets

(51) Int. Cl.
*F16C 1/20* (2006.01)
*A61B 1/00* (2006.01)
*A61B 17/00* (2006.01)
*A61M 25/09* (2006.01)

(52) U.S. Cl.
CPC ............... *A61B 1/00* (2013.01); *A61B 17/00* (2013.01); *A61M 2025/09191* (2013.01); *D07B 1/0633* (2013.01); *D07B 1/0646* (2013.01); *D07B 2201/204* (2013.01); *D07B 2201/2008* (2013.01); *D07B 2201/2021* (2013.01); *D07B 2201/2039* (2013.01); *D07B 2201/2059* (2013.01); *D07B 2205/3028* (2013.01); *D07B 2205/3032* (2013.01); *D07B 2207/4063* (2013.01); *D07B 2207/4072* (2013.01); *D07B 2501/2084* (2013.01)

(58) Field of Classification Search
USPC .......................................................... 57/213
See application file for complete search history.

(56) References Cited

U.S. PATENT DOCUMENTS

| | | | | |
|---|---|---|---|---|
| 5,609,014 A * | 3/1997 | Obara | ................. | D07B 1/0626 57/212 |
| 5,766,184 A | 6/1998 | Matsuno et al. | | |
| 6,023,026 A * | 2/2000 | Funahashi | ............ | D07B 1/0673 174/128.1 |
| 6,109,017 A * | 8/2000 | Kawatani | .............. | B60C 9/0007 152/527 |
| 6,520,232 B1 * | 2/2003 | Miyazaki | ............... | B60C 9/0007 152/451 |
| 10,426,505 B2 * | 10/2019 | Matsumoto | .......... | D07B 1/0673 |
| 2001/0018942 A1 * | 9/2001 | Miyazaki | .............. | B60C 9/0007 152/526 |
| 2002/0151823 A1 * | 10/2002 | Miyata | ................ | A61B 5/6851 600/585 |
| 2004/0116833 A1 * | 6/2004 | Kato | ................ | A61B 1/00071 600/585 |
| 2007/0289686 A1 * | 12/2007 | Sasabe | .................. | B29D 30/48 152/539 |
| 2010/0200143 A1 * | 8/2010 | Okamoto | ............... | B29D 30/48 152/539 |
| 2012/0180926 A1 * | 7/2012 | Rebouillat | ............... | D02G 3/48 152/527 |
| 2014/0295184 A1 * | 10/2014 | Grabandt | ............... | D07B 1/025 428/371 |

FOREIGN PATENT DOCUMENTS

| | | |
|---|---|---|
| JP | H01-062396 U | 4/1989 |
| JP | H05-230783 A | 9/1993 |
| JP | H08-126648 A | 5/1996 |
| JP | H08176978 | 7/1996 |
| JP | H09-256285 A | 9/1997 |
| JP | 2942885 B2 | 6/1999 |
| JP | 3101207 U | 2/2004 |
| JP | 2004277993 A | 10/2004 |
| JP | 2005-013296 A | 1/2005 |
| JP | 2006-283259 A | 10/2006 |
| JP | 2008-017954 A | 1/2008 |
| JP | 2008-155052 A | 7/2008 |
| JP | 2011-006803 A | 1/2011 |
| JP | 2011-202321 A | 10/2011 |
| JP | 2012-082530 A | 4/2012 |
| JP | 2012-157378 A | 8/2012 |

* cited by examiner

MANIPULATION ROPE

TECHNICAL FIELD

The present invention relates to manipulation ropes that can be used also for, for example, medical instruments.

BACKGROUND ART

As a medical instrument equipped with a manipulation rope, for example, an endoscope treatment instrument disclosed in JPH8-126648 is known. In the endoscope treatment instrument, an operation unit being held by hand and a treatment unit provided at its leading end are connected by a manipulation wire rope having torque transmittability. An operator inserts the treatment unit into a body cavity of a patient and operates the operation unit, whereby an operating force thereof is transmitted to the treatment unit by the manipulation wire rope. The manipulation wire rope allows a pushing force, a pulling force, and a rotational force (torque) to be transmitted from the operation unit to the treatment unit. By the transmitted force, a portion, of a body, to be treated can be subjected to medical treatment.

The manipulation wire rope is required to have not only transmittability of pushing and pulling force, but also an excellent torque transmittability (rotation followability) according to application of the manipulation wire rope. In a case where a torque transmittability or the like of the manipulation wire rope is insufficient, an operation of the operation unit is not reproduced by the treatment unit. Furthermore, particularly in the field of medical devices, the manipulation wire rope is required to have flexibility according to the diameter of the medical device being reduced.

A manipulation wire rope used for a medical treatment instrument is disclosed in JP2005-13296. The wire rope is structured such that, by, for example, wires in the outer layer and wires in the inner layer being stranded in a parallel lay, the wires adjacent to each other are brought into contact with each other as closely as possible along the rope longitudinal direction. This structure is adopted in order to inhibit reduction of an operating force and an operation amount from an operation unit to a treatment unit.

In Japanese Utility Model Registration No. 3101207, a manipulation wire rope which can be used in various fields is disclosed. In the manipulation wire rope, the forming rate is not less than 90% and not greater than 95%, This is for inhibiting wires of the rope from being damaged due to friction and improving resistance to bending fatigue.

Further, JPH5-230783 discloses a manipulation wire rope used in automobile window regulators and a wide range of various other fields. In the manipulation wire rope, the forming rate is not less than 65% and not greater than 90%. This is for preventing deformation and inhibiting the wires from being secondarily bent, without reducing resistance to bending fatigue in the rope. In JPH5-230783 and Japanese Utility Model Registration No. 3101207, measures for improving torque transrrdttability or the like are not described.

CITATION LIST

Patent Literature

Patent Literature 1: JPH8-126648
Patent Literature 2: JP2005-13296
Patent Literature 3: Japanese Utility Model Registration No. 3101207
Patent Literature 4: JPH5-23G783

SUMMARY OF THE INVENTION

Problems to be Solved by the Invention

The present invention is made in view of the aforementioned circumstances, and an object of the present invention is to provide a manipulation rope having an excellent torque transmittability.

Solution to the Problems

A manipulation rope of the present invention includes a side wire or a side strand which is an outermost layer, the side wire or the side strand having a forming rate that is greater than 100% and not greater than 110%.

Preferably, the side wire or the side strand having been formed has a spiral, shape in which a flatness that is an aspect ratio obtained by a major axis being divided by a minor axis is not less than 1.01 and not greater than 1.10.

Preferably, an elongation of the rope at a time when a tensile load that is 1.0% of a breaking load is applied, is not less than 0.04% and not greater than 0.10%.

Preferably, the forming rate is not less than 101% and not greater than 105%.

Preferably, the flatness is not less than 1.01 and not greater than 1.05.

Preferably, a strand angle of the side wire or the side strand having been formed is not less than 15°.

Advantageous Effects of the Invention

The manipulation rope of the present invention has an excellent torque transraittability.

DESCRIPTION OF EMBODIMENTS

Figure 1:
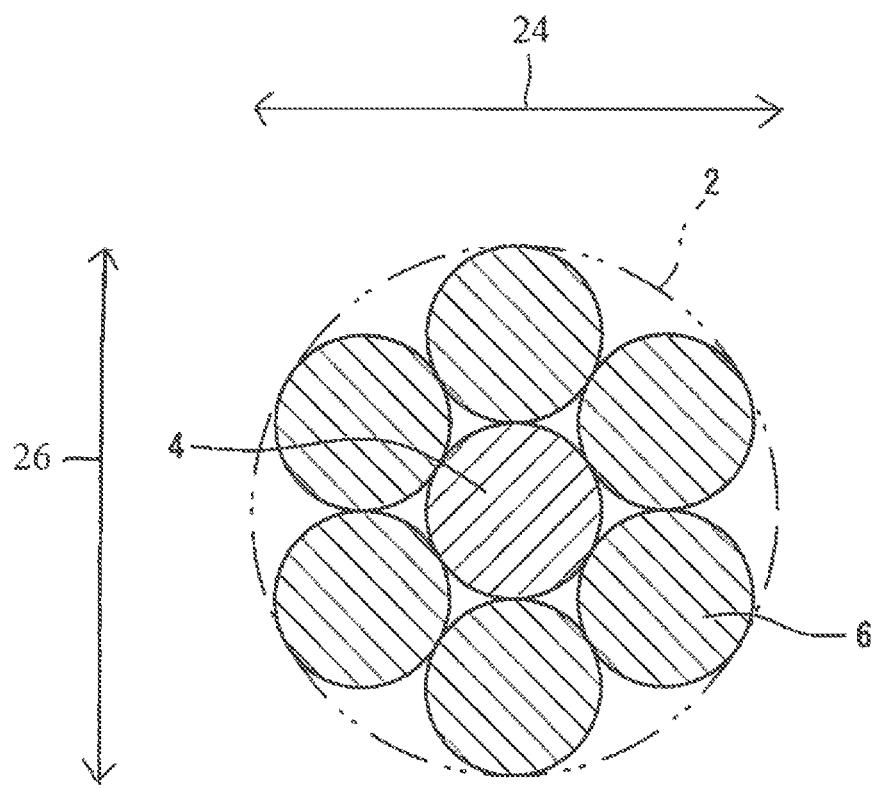
FIG. 1 is a transverse cross-sectional view of a manipulation rope according to one embodiment of the present invention.
Figure 2:
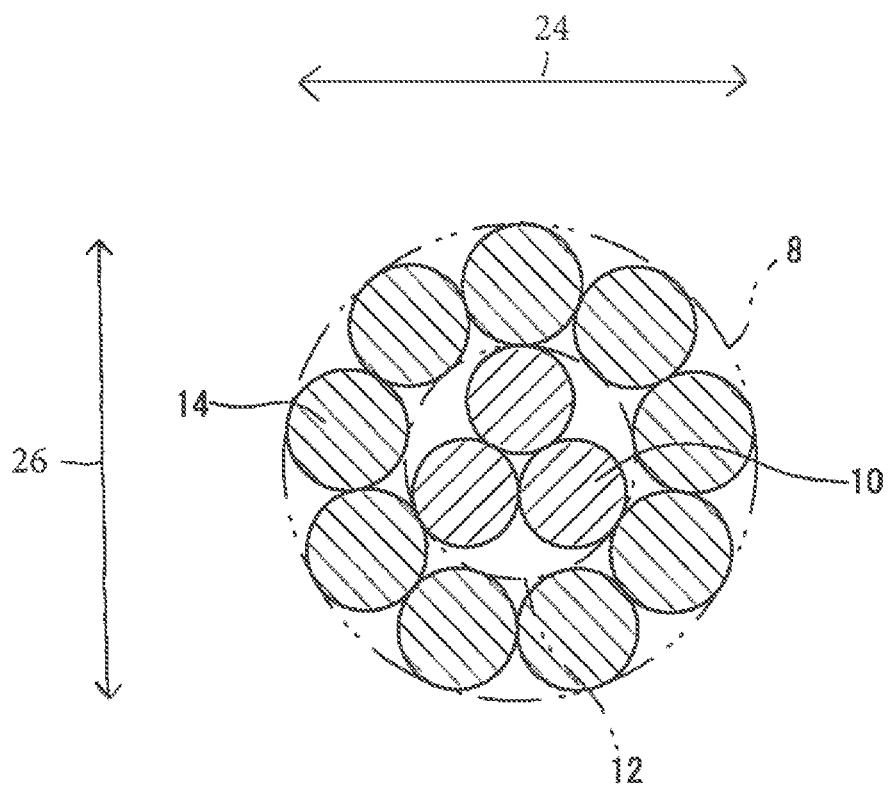
FIG. 2 is a transverse cross-sectional view of a manipulation rope according to another embodiment of the present invention.
Figure 3:
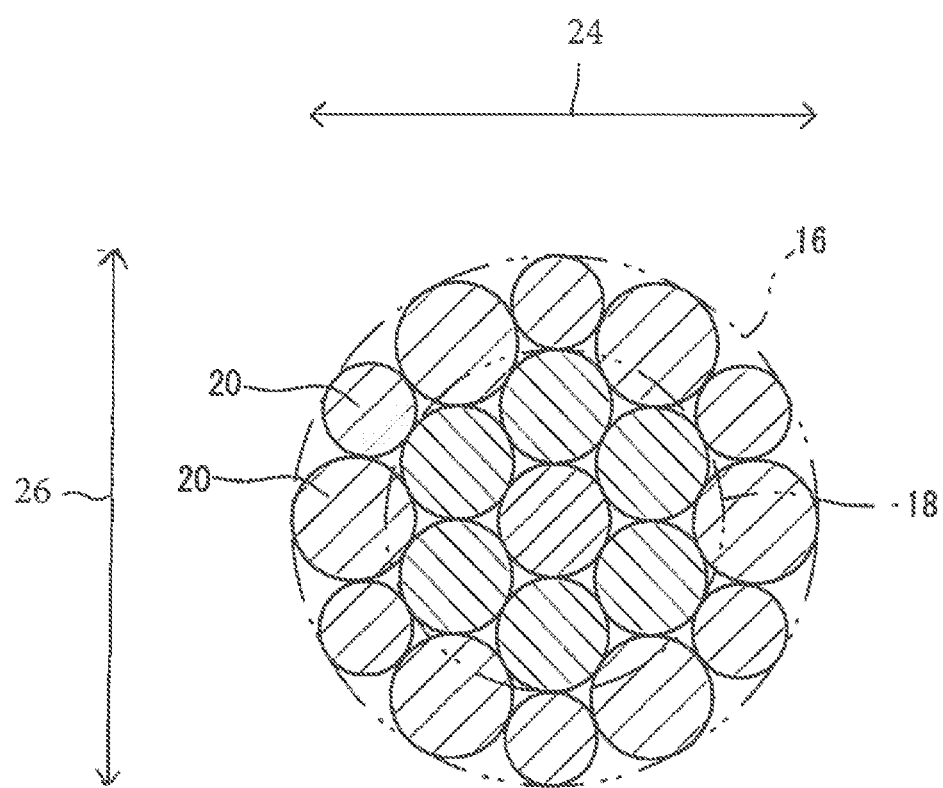
FIG. 3 is a transverse cross-sectional view of a manipulation rope according to still another embodiment of the present invention.

The following will describe in detail the present invention based on preferred embodiments with reference where appropriate to the accompanying drawing, FIG. 1 to FIG. 3 illustrate a plurality of examples of manipulation wire ropes (hereinafter, each simply referred to also as rope) according to the present invention. Ropes 2, 8, 16 each include a strand obtained by a plurality of wires being stranded. The present invention is not limited to the structure of the embodiment shown in each of FIG. 1 to FIG. 3.

The rope 2 shown in FIG. 1 has a 1+6 layer stranded structure which includes one core wire (core) 4 and six wires (each of which is also referred to as side wire) 6 in the outermost layer. The rope 8 shown in FIG. 2 has a 3+9 layer stranded structure which includes a core strand 12 formed from three wires 10 and nine side wires 14. The rope 16 shown in FIG. 3 has a 1+6+12 layer stranded structure which includes: a core strand 18 which is a 1+6 layer stranded inner layer; and 12 side wires 20. In the rope 16, the side wires 20 have different diameters such that the transverse cross-sectional shape of the rope 16 is close to a circular shape. However, the rope 16 is not limited to one having such a structure, and all the side wires 20 may have the equal diameter. The rope 2, 8, 16 has a stranded structure suitable to a manipulation rope used for a medical instrument. However, the rope 2, 8, 16 is not limited to such a manipulation rope.

The rope 2, 8, 16 of the embodiment can be used for a medical instrument. The rope is attached to a medical instrument for manipulation such that, for example, the proximal end portion of the rope is connected to an operation unit, being held by hand, of the medical instrument, and the leading end portion of the rope is connected to a treatment unit. Torque and pushing and pulling force applied to the proximal end portion are transmitted to the leading end portion, and the treatment unit is allowed to perform a treatment operation.

In the present embodiment, the wire of the rope 2, 8, 16 is formed from an austenitic stainless steel such as SUS304 and SUS316, a nickel-titanium alloy, or the like. Needless to say, the material of the wire is not limited to such a material. The tensile strength of the material of the wire is preferably not less than 2000 MPa, more preferably not less than 2500 MPa, and particularly preferably not less than 2800 MPa.

A forming rate of the side wire 6, 14, 20 or the side strand which is the outermost layer of the rope 2, 8, 16, is greater than 100% and not greater than 110%. The forming rate is calculated in such a manner that the diameter (waviness diameter) of a spiral shape cf the side wire or the side strand in a state where the rope is disassembled (disentangled), is divided by an actually measured outer diameter of the rope, and the obtained value is represented by a percentage as the forming rate. When the forming rate is in the above-described range, the rope becomes flexible and is easily bent. Further, friction between the side wires or between the side strands is increased, and friction between the side wire or the side strand and the core wire or the core strand is reduced, thereby reducing energy loss in transmission of rotation of the rope. It has been found that, by this action, transmission of rotational force from the proximal end to the leading end is facilitated, and torque transmittability is improved. Meanwhile, when the forming rate is not greater than 100%, since friction between the side wire or the side strand and the core wire or the core strand is increased, energy loss in transmission of rotation of the rope may be increased. Further, when the forming rate is greater than 110%, a so-called open structure in which a gap is generated between the wires is likely to be caused, and the diameter of the rope may not be obtained as desired. In this viewpoint, the forming rate is preferably not less than 101% and preferably not greater than 105%.

The spiral of the side wire or the side strand is not completely circular but ellipsoidal or oval in some cases. In these cases, the spiral is a so-called flattened spiral. In this case, as the waviness diameter by which the forming rate is determined, the major axis among the major axis and the minor axis is used. Also when the major axis is used as the waviness diameter, the rope 2, 8, 16 is formed such that the forming rate is not greater than 110%. Further, if the minor axis is used as the waviness diameter, the rope 2, 8, 16 is formed such that the forming rate is greater than 100%.

In the side wire 6, 14, 20 or the side strand which is the outermost layer of the rope 2, 8, 16, the flatness (also referred to as aspect ratio) is preferably not less than 1.01 and preferably not greater than 1.10. The flatness represents an aspect ratio, of the above-described flattened spiral of the disentangled side wire or side strand, obtained by dividing the major axis by the minor axis. An example of a method for measuring the diameter of the spiral will be described below. On a projector, the disentangled side wire or side strand is rotated around the center axis thereof. In this process, the diameters of the spiral are measured at any plurality of angular positions (for example, five positions). The plurality of angular positions are preferably spaced from each other at equiangular intervals. The greatest value among the plurality of measured values is determined as the major axis. The diameter of the spiral which is measured in the direction obtained by 90° phase rotation around the center axis of the side wire or the side strand being performed from the direction in which the major axis 24 is measured, is determined as the minor axis 26. In the disentangled side wire or side strand, a plurality of spirals are formed continuously along the axial direction thereof. Therefore, as each diameter in the 90° intersecting direction, an average of a plurality of measured values (for example, at any 10 positions) is adopted.

When the flatness is less than 1.01, friction between the side wire or the side strand and the core wire or the core strand is increased, so that energy loss in transmission of rotation of the rope may be increased. Meanwhile, when the flatness is greater than 1.10, a so-called open structure is caused, and the rope may be difficult to stably manufacture. In this viewpoint, the flatness Is preferably not less than 1.01 and preferably not greater than 1.05.

When the forming rate of the side wire or the side strand is in the above-described range, flexibility, bendability, and transmittability of rotational force in the rope are improved as described above. In addition thereto, it has been found that, when the flatness is in the above-described range, flexibility, bendability, and transmittability of rotational force in the rope are further improved.

An initial elongation of the rope 2, 8, 16 is preferably not less than 0.04% and preferably not greater than 0.10%. The initial elongation of the rope is obtained by an elongation (increase rate of length) of a rope at a time when a tensile load that is 1.0% of a breaking load of the rope is applied being represented as a percentage.

The rope having a great initial elongation is flexible and easily bent. That is, the rope having a great initial elongation has a small longitudinal elastic modulus (Young's modulus). When the initial elongation is less than 0.04%, friction between the side wire or the side strand and the core wire or the core strand is increased, so that energy loss in transmission of rotation of the rope may be increased. Meanwhile, when the initial elongation is greater than 0.10%, the rope tends to have a so-called open structure, and the rope may be difficult to stably manufacture.

The initial elongation is confirmed by a tensile testing for a rope to be tested. The tensile testing can be performed in compliance with the standard of JISZ2241 (2011). Initially, a breaking load of the rope to be tested is measured. Then, the rope to be tested is attached to the tester, and a tensile load is applied thereto. At a time when the tensile load becomes 1.0% of the breaking load, increase of the gauge length that is set in the axial direction of the rope to be tested is measured. The percentage of the increase relative to the original gauge length is set as the initial elongation.

A strand angle of the side wire 6, 14, 20 or the side strand of the rope 2, 8, 16 is preferably not less than 15°. In the rope in which the strand angle is not less than 15°, the initial elongation that is not less than 0.04% can be easily obtained. The strand angle is an angle between the wire or the strand, and the center axis of the rope or the strand. In the description herein, the strand angle is an angle between the side wire or the side strand, and the center axis of the rope.

A process for manufacturing the rope will be briefly described below. Initially, each wire of the rope is adjusted in the wire drawing process step such that a required tensile strength can be obtained. Then, preforming is performed for the side wire or the side strand by a preformer in the wire stranding process step such that required forming rate and flatness can be obtained. In particular, the preforming is performed such that the spiral of the side wire or the side strand has a flattened transverse cross-section. In the heat treatment process step for the rope, not batch processing but continuous processing is performed. Specifically, the rope, to be processed, which passes through a heat treatment furnace is tensioned at an inlet and an outlet of the heat treatment furnace. Thus, the straightness of the rope is improved. Further, the forming rate and the flatness of the side wire or the side strand are determined.

EXAMPLES

Hereinafter, effects of the present, invention will become apparent according to examples. However, the present invention should not be restrictively construed based on the description of examples.

Examples 1 to 12

Manipulation wire ropes of examples 1 to 12 each having the structure shown in FIG. 1 were obtained. Each of the ropes was a wire rope for a medical device. A material of each of the wires was SUS304 austenitic stainless steel. The outer diameter (cord diameter) of the rope was 0.7 mm, the outer diameter of the core wire was 0.25 mm, and the outer diameter of the side wire was 0.23 mm. Each wire had the tensile strength of 2850 MPs. Each rope had a 1+6 layer stranded structure, and a stranding pitch in each rope was 5.5 mm. The temperature in the heat treatment for the rope of each of examples 1 to 12 was 500° C. The forming rate, the flatness, and the initial elongation of the side wire of the rope of each of examples 1 to 12 were as indicated in Table 1 and Table 2.

Comparative Example 1

A manipulation wire rope of comparative example 1 was obtained in the same manner as in example 1 except that the forming rate, the flatness, and the initial elongation were as indicated in Table 2, and the diameter of the cord was much greater than 0.7 mm. As indicated in Table 2, the forming rate of the rope of comparative example 1 was 115%, and a so-called open, structure in which multiple gaps were generated among the wires, was caused. Therefore, the diameter of the cord was much greater than 0.7 mm. Such a rope of comparative example 1 was not suitable as a manipulation wire rope for a medical device, and it was determined that this rope was not able to be used as a manipulation wire rope for a medical device.

Comparative Example 2

Comparative example 2 was a manipulation wire rope according to conventional art. The manipulation wire rope of comparative example 2 was the same as in example 1 except that the forming rate, the flatness, and initial elongation were as indicated in Table 2. The side wire of the rope of comparative example 2 was not formed so as to be flattened.

TABLE 1

| Evaluation of torque transmittability | | | | | | | |
|---|---|---|---|---|---|---|---|
| | Ex. 1 | Ex. 2 | Ex. 3 | Ex. 4 | Ex. 5 | Ex. 6 | Ex. 7 |
| Forming rate (%) | 100.5 | 101 | 101 | 101 | 101 | 101 | 101 |
| Flatness | 1.01 | 1.00 | 1.005 | 1.05 | 1.01 | 1.01 | 1.01 |
| Initial elongation (%) | 0.05 | 0.05 | 0.05 | 0.05 | 0.03 | 0.04 | 0.10 |
| Torque transmittability (index) | 58.8 | 58.0 | 46.9 | 27.2 | 51.9 | 37.0 | 28.4 |

TABLE 2

| Evaluation of torque transmittability | | | | | | | |
|---|---|---|---|---|---|---|---|
| | Ex. 8 | Ex. 9 | Ex. 10 | Ex. 11 | Ex. 12 | Comp. Ex. 1 | Comp. Ex. 2 |
| Forming rate (%) | 101 | 101 | 102 | 105 | 110 | 115 | 99 |
| Flatness | 1.01 | 1.10 | 1.02 | 1.01 | 1.01 | 1.01 | 1.00 |
| Initial elongation (%) | 0.05 | 0.05 | 0.07 | 0.05 | 0.05 | 0.05 | 0.03 |
| Torque transmittability (index) | 26.4 | 39.5 | 25.1 | 33.3 | 46.9 | Not usable | 100 |

Evaluation of Torque Transmittability

Torque transmittability is evaluated on the basis of difference, between a rotation angle on the proximal end side (corresponding to the operation unit) and a rotation angle on the leading end side (corresponding to the treatment unit), obtained when the proximal end side portion of each rope was rotated. For the rope of each of examples and comparative examples, the following torque transmittability evaluation test was performed.

Figure 4:
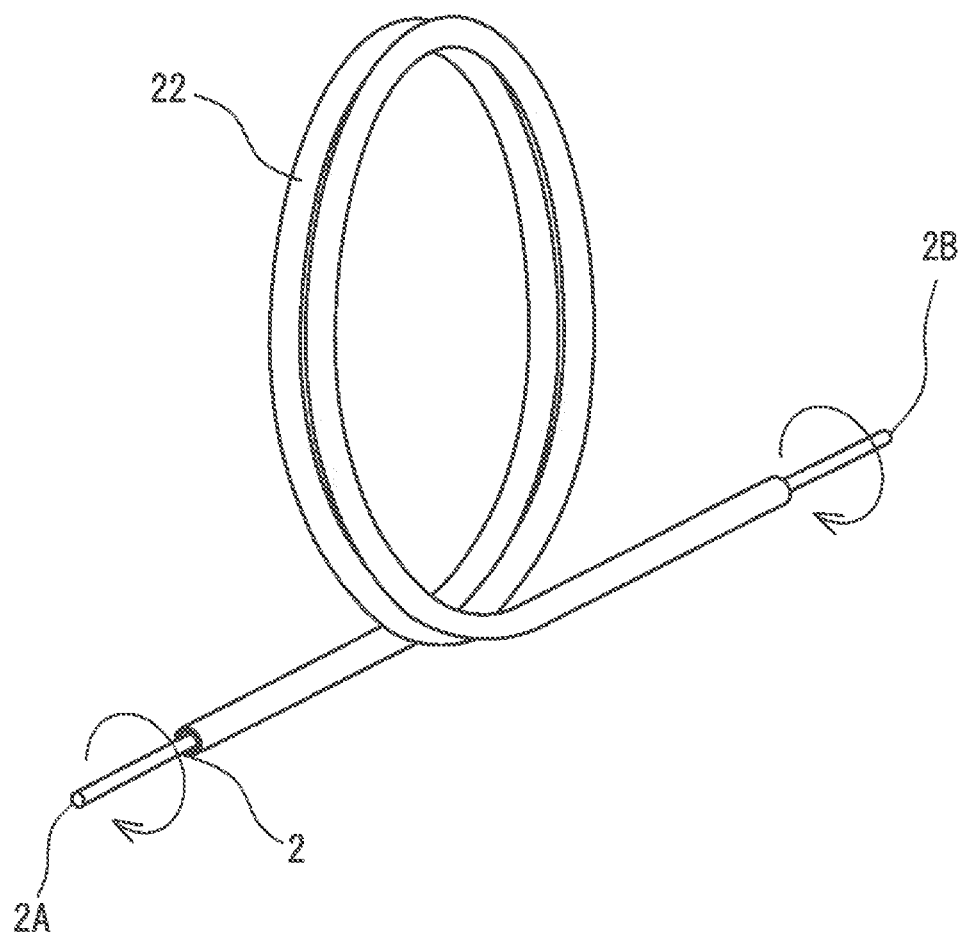
FIG. 4 is a perspective view illustrating an outline of a torque transmittability evaluation testing method for a manipulation rope.

As shown in FIG. 4, a dual spiral having the diameter of 200 mm was formed in the rope of each of examples 1 to 12 and comparative examples 1, 2. The dual spiral was formed by, for example, a rope 2 to be tested being inserted into a small-diameter pipe 22 which had a dual spiral shape having the diameter of 200 mm so as to be straight on both end sides. A rotational force around the center axis was applied to the proximal end side portion of the rope 2 to be tested, in a state where the rope 2 to be tested was inserted in the small-diameter pipe 22. While the rotational force was applied, a rotation angle on a proximal end side 2A of the rope 2 and a rotation angle on a leading end side 2B thereof were simultaneously measured.

Figure 5:
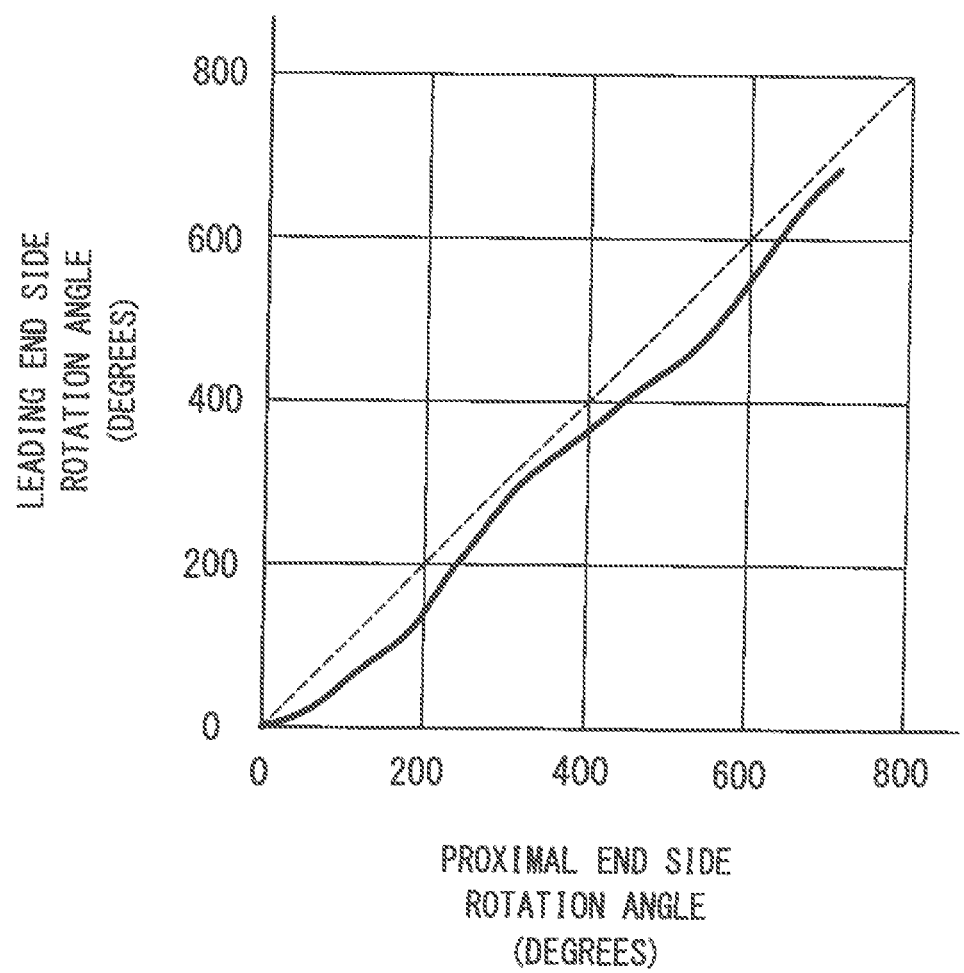
FIG. 5 shows a graph in which a rotation angle of a manipulation rope on a proximal end side and a rotation angle thereof on the leading end side at the same point of time are associated with each other.
Figure 6:
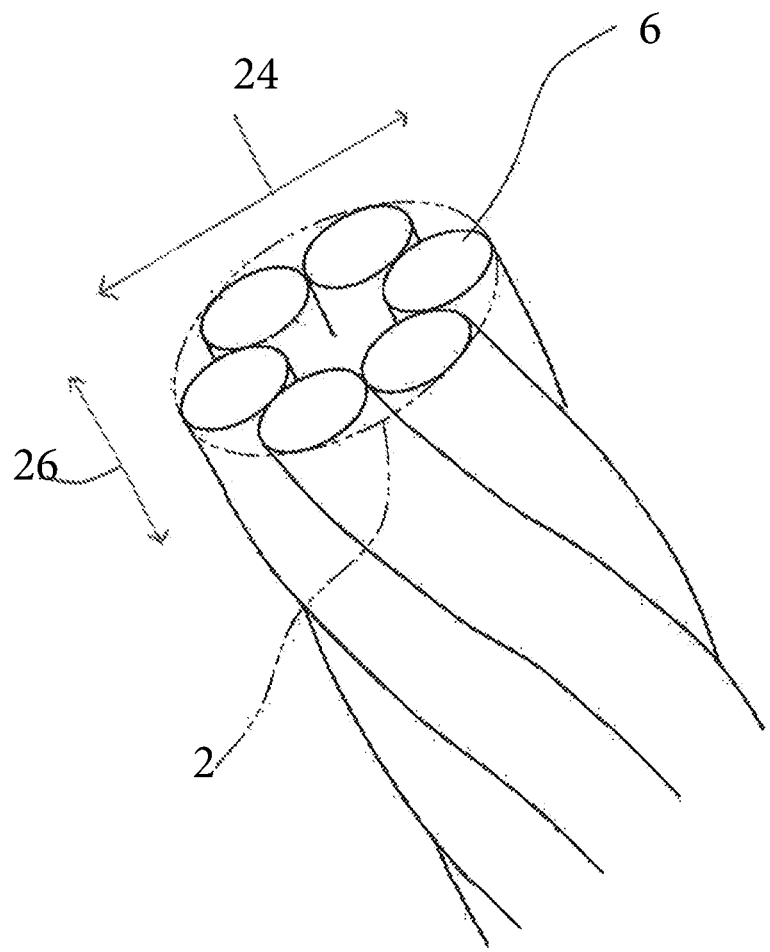
FIG. 6 is a perspective view of the manipulation rope.

FIG. 5 shows a graph in which the rotation angle on the proximal end side of the rope and the rotation angle on the leading end side thereof at the same point of time are associated with each other. In other words, FIG. 5 is a graph indicating a relationship between an input rotation angle and an output rotation angle in the manipulation rope. The unit of the angle is degree (°). In the graph, a broken line that extends from the originating point of 0° so as to be tilted by 45° relative to the horizontal axis and the vertical axis represents a straight line that indicates that difference between the rotation angle on the proximal end side and the rotation angle on the leading end side is zero in a range of all the measured angles (range in which the input rotation angle is from 0° to about 720°). The difference, to be evaluated for the rope to be tested, between the rotation angle on the proximal end side and the rotation angle on the leading end side is represented as difference in the vertical axis direction between the 45° titled straight line and the measured value curve in the drawing. The difference in the rotation angle corresponds to the rotation angle on the proximal end side. In the drawing, for easy understanding, the difference in the rotation angle is indicated so as to be greater than the actual one. In the range in which the input rotation angle is from 0° to 720°, the greatest angular difference among the measured differences in the rotation angle is evaluated.

The greatest angular difference in the rope of each of examples 1 to 12 and comparative examples 1, 2 is indicated in Table 1 and Table 2 as an index with the greatest angular difference of comparative example 2 being 100. The less the greatest angular difference is, the lees the value of the index is and the more excellent the torque transmittability is.

As indicated in Table 1 and Table 2, the evaluation result clearly indicates that the present invention is superior.

INDUSTRIAL APPLICABILITY

The manipulation rope of the present invention is advantageously used as a manipulation rope for a medical instrument.

DESCRIPTION OF THE REFERENCE CHARACTERS 2, 8, 16 . . . manipulation wire rope
4 . . . core wire
6, 14, 20 . . . side wire
10 . . . wire
12, 18 . . . core strand

The invention claimed is:

1. A manipulation rope comprising a core wire or core strand and a side wire or a side strand which is an outermost layer around the core wire or core strand, wherein a preformed side wire or the side strand has a forming rate that is greater than 100% and not greater than 110%, where the preformed side wire or side strand is formed in a state that is disassembled without the core wire or core strand of said manipulation rope and where the preformed side wire or side strand has a flattened spiral shape, the forming rate is represented as a percentage obtained by a waviness diameter of the spiral shape of the preformed side wire or side strand in the disassembled state divided by a measured outer diameter of the rope, and where the manipulation rope is configured for transmitting torque when rotated around an axis of the manipulation rope, and where an assembled core wire or core strand and the side wire or side strand pass through a heat treating furnace while tensioned at an inlet and an outlet of the heat treatment furnace, and subjected to continuous heat treatment processing in the heat treatment furnace to obtain the manipulation rope.

2. The manipulation rope according to claim 1, wherein the preformed side wire or the side strand having been formed has a spiral shape where the flattened spiral shape has an aspect ratio obtained by a major axis of said side wire or side strand being divided by a minor axis of said side wire or side strand is not less than 1.01 and not greater than 1.10.

3. The manipulation rope according to claim 1, wherein an elongation of said manipulation rope at a time when a tensile load of the manipulation rope that is 1.0% of a breaking load is applied, is not less than 0.04% and not greater than 0.10%.

4. The manipulation rope according to claim 1, wherein the forming rate of said preformed side wire or side strand is not less than 101% and not greater than 105%.

5. The manipulation rope according to claim 2, wherein the aspect ratio of said preformed side wire or side strand is not less than 1.01 and not greater than 1.05.

6. The manipulation rope according to claim 1, wherein a strand angle of the preformed side wire or the side strand having been formed is not less than 15°.

* * * * *